(12) United States Patent
Olson (10) Patent No.: US 9,839,232 B2
(45) Date of Patent: Dec. 12, 2017

(54) STABLE THICKENER FORMULATIONS

(71) Applicant: NESTEC S.A., Vevey (CH)

(72) Inventor: Erin Olson, Plymouth, MN (US)

(73) Assignee: Nestec S.A., Vevey (CH)

(*) Notice: Subject to any disclaimer, the term of this patent is extended or adjusted under 35 U.S.C. 154(b) by 0 days.

(21) Appl. No.: 14/612,847

(22) Filed: Feb. 3, 2015

(65) Prior Publication Data

US 2015/0147432 A1 May 28, 2015

Related U.S. Application Data

(62) Division of application No. 13/504,361, filed as application No. PCT/US2010/053891 on Oct. 25, 2010.

(60) Provisional application No. 61/254,858, filed on Oct. 26, 2009, provisional application No. 61/394,368, filed on Oct. 19, 2010.

(51) Int. Cl.

| *A23L 1/054* | (2006.01) |
|---|---|
| *A23L 1/29* | (2006.01) |
| *A23L 1/0532* | (2006.01) |
| *A23L 1/0522* | (2006.01) |
| *A23L 33/00* | (2016.01) |
| *A61K 9/00* | (2006.01) |
| *A61K 31/00* | (2006.01) |
| *A23L 29/212* | (2016.01) |
| *A23L 29/219* | (2016.01) |
| *A23L 29/256* | (2016.01) |
| *A23L 29/269* | (2016.01) |
| *A61K 47/36* | (2006.01) |

(52) U.S. Cl.
CPC ............ *A23L 33/40* (2016.08); *A23L 29/212* (2016.08); *A23L 29/219* (2016.08); *A23L 29/256* (2016.08); *A23L 29/27* (2016.08); *A23L 33/30* (2016.08); *A61K 9/0053* (2013.01); *A61K 31/00* (2013.01); *A23V 2002/00* (2013.01); *A61K 47/36* (2013.01)

(58) Field of Classification Search
None
See application file for complete search history.

(56) References Cited

U.S. PATENT DOCUMENTS

| 4,105,461 A | 8/1978 | Racciato |
| 4,232,049 A | 11/1980 | Blake |
| 4,623,552 A | 11/1986 | Rapp |
| 5,922,391 A | 7/1999 | Trueck |
| 6,139,895 A | 10/2000 | Zablocki et al. |
| 6,893,675 B1 | 5/2005 | Jacobson et al. |
| 2004/0028795 A1 | 2/2004 | Doat et al. |
| 2004/0197456 A1 | 10/2004 | Holahan |
| 2004/0258823 A1* | 12/2004 | Dufresne ............... A21D 2/00 426/573 |

FOREIGN PATENT DOCUMENTS

| EP | 0022558 | 1/1981 |
| EP | 0274348 | 7/1988 |
| EP | 2551818 | 1/2013 |
| FR | 2847770 | 6/2004 |
| JP | 2006141207 | 6/2006 |
| JP | WO 2009/044538 | * 4/2009 ............ A23L 1/212 |
| WO | 0066633 | 11/2000 |
| WO | WO2004049822 | 6/2004 |
| WO | WO2006054886 | 5/2006 |
| WO | WO2008137181 | 11/2008 |

OTHER PUBLICATIONS

Mottar, The Use of Wheat Starch in UHT Milk Desserts, Food Ingredients Europe:; Conference Proceedings 1989, Porte De Versailles, Paris, Sep. 27, 28, 29, 1989, pp. 108-111.*
Self Nutrition Data, Nutrition Facts: Milk, whole, 3.25% milkfat, SelfNutritionData, Accessed Apr. 24, 2014, online at: nutritiondata.self.com/facts/dairy-and-egg-products/69/2.*
Ney et al., Senescent Swallowing: Impact, Strategies and Interventions, Nutr Clin Pract., 2009, 24(3): pp. 395-413.*
"Swallowing Assisting Food," Derwent, 2003, XP002334599, one page.
Search Report for International Application No. PCT/US2010/053891 dated May 9, 2011.
Written Opinion for International Application No. PCT/US2010/053891 dated May 9, 2011.
Cole-Parmer's FoodTechSource, Viscosity, 2002, acessed online at: www.foodtechsource.com/rcenter/tech_data/td_viscosity.htm.
Conde Nast, Nutrition Facts: Cream, fluid, heavy whipping, SelfNutritionData, 2012, accessed online at: nutritiondata.self.com/facts/dairy-and-egg-products/21/2.
Harlan Bros. Production, LLC, Ingredients: Yogurt, D. Gourmet, Jan. 10, 2013, accessed online at: www.drgourmet.com/ingredients/yogurt.shtml.
Rofes et al., Pathophysiology of oropharyngeal dysphagia in the frail elderly, Neurogastroenterology & Motiliy (2010) 22, 851-e230.
Appelqvist et al. "Starch-Biopolymer Interactions—A Review" Food Reviews International, 1997, vol. 13, 3 pages.

* cited by examiner

*Primary Examiner* — Karen Cochrane Carlson
*Assistant Examiner* — Jennifer M. H. Tichy
(74) *Attorney, Agent, or Firm* — K&L Gates LLP (57) ABSTRACT

Stable thickener formulations and nutritional compositions having the stable thickener formulations are provided. In a general embodiment the present disclosure provides a stable thickener formulation comprising from about 0.015% to about 0.05% by weight of carrageenan and from about 1.2% to about 4.0% by weight of starch. The stable thickener formulation can be used in nutritional compositions used to treat a variety of physiological conditions.

17 Claims, 6 Drawing Sheets

STABLE THICKENER FORMULATIONS

CROSS REFERENCE TO RELATED APPLICATIONS

This application is a divisional of U.S. application Ser. No. 13/504,361, filed May 3, 2012, which is a National Stage of International Application No. PCT/US10/053891, filed on Oct. 25, 2010, which claims priority to U.S. Patent Application No. 61/254,858, filed Oct. 26, 2009, which claims priority to U.S. Patent Application No. 61/394,368, filed Oct. 19, 2010, the entire contents of which are incorporated herein by reference.

BACKGROUND

The present disclosure generally relates to health and nutrition. More specifically, the present disclosure relates to stable thickener formulations for nutritional compositions.

There are many types of nutritional compositions currently on the market. Nutritional compositions can be targeted toward certain consumer types, for example, young, elderly, athletic, etc., based on the specific ingredients of the nutritional composition. Nutritional compositions can also be formulated based on the certain physiological conditions that the nutritional compositions are intended to treat or improve.

Dysphagia is the medical term for the symptom of difficulty in swallowing. Esophageal dysphagia affects a large number of individuals of all ages, but is generally treatable with medications and is considered a less serious form of dysphagia. Esophageal dysphagia is often a consequence of mucosal, mediastinal, or neuromuscular diseases.

Oral pharyngeal dysphagia, on the other hand, is a very serious condition and is generally not treatable with medication. Oral pharyngeal dysphagia also affects individuals of all ages, but is more prevalent in older individuals. Oral pharyngeal dysphagia is often a consequence of an acute event, such as a stroke, brain injury, or surgery for oral or throat cancer. In addition, radiotherapy and chemotherapy may weaken the muscles and degrade the nerves associated with the physiology and nervous innervations of the swallow reflex. It is also common for individuals with progressive neuromuscular diseases, such as Parkinson's Disease, to experience increasing difficulty in swallowing initiation.

The consequences of untreated or poorly managed oral pharyngeal dysphagia can be severe, including dehydration, malnutrition leading to dysfunctional immune response, and reduced functionality, airway obstruction with solid foods (choking), and airway aspiration of liquids and semi-solid foods, promoting aspiration pneumonia and/or pneumonitis. Severe oral pharyngeal dysphagia may require nutrition to be supplied by tube feeding.

Mild to moderate oral pharyngeal dysphagia may require the texture of foods to be modified in order to minimize the likelihood of choking or aspiration. This may include the thickening of liquids and/or pureeing of solid foods, both of which have been shown to be the most effective means of preventing choking and aspiration during the eating process. Thickened liquids are designed to have three properties: (i) a more cohesive bolus that can be maintained throughout the action of swallowing, (ii) slower delivery to the throat, thereby compensating for the increased period in which the swallowing reflexes prepare for the thickened liquid, and (iii) provide greater density to increase awareness of the presence of food or liquid bolus in the mouth.

Thickened nutritional formulations can also be used as part of therapies to treat other physiological conditions or disease such as renal failure, chronic obstructive pulmonary disorders, malabsorption disorders, etc.

SUMMARY

Stable thickener formulations and nutritional compositions having the stable thickener formulations are provided. In a general embodiment, the present disclosure provides a nutritional composition including a stable thickener formulation. The stable thickener formulation can include specific ranges of carrageenan and starch that provide a consistent viscosity of the nutritional composition during an extended storage time and at different temperatures. By adding carrageenan, the starch level can be decreased. Also, the viscosity increase of nutritional compositions at refrigerated storage temperatures can be minimized when carrageenan and/or xanthan is added thereto. The stable thickener formulations can also include specific amounts of xanthan gum and starch that provide a stable viscosity. The nutritional composition can be a complete feeding or an oral nutritional supplement.

In addition, Applicant has found that the amounts of carrageenan and/or xanthan required for a thickener formula depends on the formulation of the nutritional composition and the final amount and type of protein therein. Indeed, Applicant has found that the amounts and type of proteins found in a nutritional composition can affect the amount of carrageenan and starch required for the present thickener formulas, as will be discussed further below.

In an embodiment, the present disclosure provides a stable thickener formulation including from about 0.03% to about 0.05% by weight of carrageenan and from about 3.45% to about 3.65% by weight of starch. In an embodiment, the carrageenan is about 0.04% by weight and the starch is about 3.54% by weight. This stable thickener formulation can provide a viscosity or consistency similar to honey. The stable thickener formulation can further include a viscosity, at refrigerated temperatures, ranging from about 1100 cps to about 9000 cps, or from about 1100 cps to about 6000 cps, or from about 1100 cps to about 4000 cps. In another embodiment, a 1.2 cal, 14 g protein formulation could have carrageenan in an amount from about 0.02 to about 0.055% and starch in an amount from 1.0 to about 6%. Alternatively, in another embodiment, a 1.5 cal, 18 g protein formulation could have about 0.02% carrageenan or from about 0.015 to about 0.055% to carrageenan, and starch in an amount of about 0.5 to about 5%.

In another embodiment, the present disclosure provides a stable thickener formulation including from about 0.1% to about 0.14% by weight of xanthan gum and from about 2.5% to about 2.7% by weight of starch. In this embodiment, the xanthan gum is able to thicken a product pre-sterilization, while the resulting product is still thin enough to be pumped around the manufacturing plant. In another embodiment, the xanthan gum is about 0.12% by weight and the starch is about 2.6% by weight. The stable thickener formulation can further include a viscosity, at refrigerated temperatures, ranging from about 1100 cps to about 9000 cps, or from about 1100 cps to about 6000 cps, or from about 1100 cps to about 4000 cps.

In yet another embodiment, the present disclosure provides a stable thickener formulation including from about 0.03% to about 0.05% by weight of carrageenan and from about 1.7% to about 1.9% by weight of starch. In an embodiment, the carrageenan is about 0.04% by weight and the starch is about 1.8% by weight. This stable thickener formulation can provide a viscosity or consistency similar to nectar. Again, these amounts depend on the formulation of a nutritional composition and the amount and type of protein contained therein. Applicant has found that the amount and type of protein affects the amount of carrageenan and starch that should be added to the nutritional composition. For example, a 1.2 cal, 14 g protein formulation could have carrageenan in an amount from about 0.02 to about 0.055%) and starch in an amount from 1.0 to about 6%. Alternatively, in another embodiment, a 1.5 cal, 18 g protein formulation could have about 0.02% carrageenan or from about 0.015 to about 0.055% carrageenan, and starch in an amount of about 0.5 to about 5%.

In still yet another embodiment, the present disclosure provides a stable thickener formulation including from about 0.03% to about 0.05% by weight of carrageenan and from about 2.1'% to about 2.2% by weight of starch. In an embodiment, the carrageenan is about 0.04% by weight and the starch is about 2.1% by weight.

In another embodiment, the present disclosure provides a stable thickener formulation including from about 0.03% to about 0.05 by weight of carrageenan and from about 2.2% to about 2.5% by weight of starch. In an embodiment, the carrageenan is about 0.04% by weight and the starch is about 2.36% by weight. This stable thickener formulation can provide a viscosity or consistency similar to honey. Again, these amounts depend on the formulation of a nutritional composition and the amount and type of protein added thereto. Applicant has found that the amount and type of protein affects the amount of carrageenan and starch added to the nutritional compositions. For example, in another embodiment, a 1.2 cal, 14 g protein formulation could have carrageenan in an amount from about 0.02 to about 0.055% and starch in an amount from 1.0 to about 6%. Alternatively, in another embodiment, a 1.5 cal, 18 g protein formulation could have about 0.02 carrageenan or from about 0.015 to about 0.055'% carrageenan, and starch in an amount of about 0.5 to about 5%.

In still another embodiment, the present disclosure provides a stable thickener formulation including from about 0.03% to about 0.05% by weight of carrageenan and from about 2.5% to about 2.9% by weight of starch.

In an alternative embodiment, the present disclosure provides a nutritional composition including one or more nutritional ingredients, from about 0.03% to about 0.05% by weight of carrageenan, and from about 3.45% to about 3.65% by weight of starch. In yet another embodiment, the present disclosure provides a nutritional composition including one or more nutritional ingredients, from about 0.1% to about 0.14% by weight of xanthan gum, and from about 2.5% to about 2.7% by weight of starch.

The nutritional compositions can be in a formulation designed for any mammal such as a human or an animal. The active or nutritional ingredients in the nutritional composition can also be provided as a modular product. A modular product can be defined as a method of delivering one or more specific nutrients as a supplement and not intended to be used for sole source nutrition. In addition, the nutritional compositions can be shelf stable and exhibit good shelf life at ambient or even above ambient temperatures that may be encountered during distribution.

The nutritional compositions can include a viscosity ranging from about 250 cps to about 15,000 cps on a Brookfield LTV viscometer, or about 50 mPa·50 s to about 1750 mPa·50 s by Rheology measurements (e.g., Physica Rheometer) at product temperatures from about 4° C. to about 25° C. and have any suitable types of nutritional ingredients. The nutritional compositions can also include a viscosity ranging from about 100 mPa·s to about 2500 mPa·s on a Physica Rheometer. The nutritional ingredients can be one or more carbohydrates and/or one or more fats. The nutrition ingredients can also be one or more synbiotics, fish oils, phytonutrients, antioxidants, vitamins, minerals or a combination thereof.

In an embodiment, the nutritional composition further includes one or more prebiotics (e.g., dead or alive). The prebiotic can be *acacia* gum, alpha glucan, arabinogalactans, beta glucan, dextrans, fructooligosaccharides, galactooligosaccharides, galactomannans, gentiooligosaccharides, glucooligosaccharides, guar gum, inulin, isomaltooligosaccharides, lactosucrose, lactulose, levan, maltodextrins, partially hydrolyzed guar gum, pecticoligosaccharides, retrograded starch, soyoligosaccharides, sugar alcohols, xylooligosaccharides, or a combination thereof.

In an embodiment, the nutritional composition further includes one or more probiotics (e.g., dead or alive). The probiotic can be *Aerococcus, Aspergillus, Bacteroides, Bifidobacterium, Candida, Clostridium, Debaromyces, Enterococcus, Fusobacterium, Lactobacillus, Lactococcus, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Saccharomyces, Staphylococcus, Streptococcus, Torulopsis, Weissella*, or a combination thereof.

In another embodiment, the nutritional composition further includes one or more amino acids. The amino acid can be isoleucine, alanine, leucine, asparagine, lysine, aspartate, methionine, cysteine, phenylalanine, glutamate, threonine, glutamine, tryptophan, glycine, valine, proline, serine, tyrosine, arginine, histidine or a combination thereof.

In still another embodiment, the present disclosure provides a method for treating a medical condition in a patient. The method comprises administering to the patient a nutritional composition including at least one nutritional ingredient, from about 0.03% to about 0.05% by weight of carrageenan, and from about 1.5% to about 3.65% by weight of starch, or about 1.5% to about 2.9% by weight of starch, or about 3.45% to about 3.65% by weight of starch.

In an embodiment, the medical condition is dysphagia, renal failure, a chronic obstructive pulmonary disorder or a malabsorption disorder. The patient can be an elderly person. The patient can also be a pediatric patient.

In an embodiment, the nutritional composition is in an administrable form such as pharmaceutical formulations, nutritional formulations, dietary supplements, functional foods, beverage products or a combination thereof.

An advantage of the present disclosure is to provide an improved thickener formulation.

Another advantage of the present disclosure is to provide a stable thickener formulation at various temperatures that maintains a relatively constant viscosity over an extended period of time.

Yet another advantage of the present disclosure is to provide an improved nutritional composition.

Still another advantage of the present disclosure is to provide a method of treating or improving an adverse physiological condition in an individual.

Additional features and advantages are described herein, and will be apparent from the following Detailed Description and the figures.

DETAILED DESCRIPTION

The present disclosure is directed to stable thickener formulations and nutritional compositions having the stable thickener formulations. The nutritional compositions can be used for the treatment of a variety of physiological conditions such as, for example, dysphagia, renal failure, chronic obstructive pulmonary disorders and malabsorption disorders.

As used in this disclosure and the appended claims, the singular forms "a" "an" and "the" include plural referents unless the context clearly dictates otherwise. Thus, for example, reference to "an amino acid" includes a mixture of two or more amino acids, and the like.

As used herein, "about" is understood to refer to numbers in a range of numerals. Moreover, all numerical ranges herein should be understood to include all integer, whole or fractions, within the range. All dosage ranges contained within this application are intended to include all numbers, whole or tractions, contained within said range.

As used herein the term "amino acid" is understood to include one or more amino acids. The amino acid can be, for example, alanine, arginine, asparagine, aspartate, citrulline, cysteine, glutamate, glutamine, glycine, histidine, hydroxyproline, hydroxyserine, hydroxytyrosine, hydroxylysine, isoleucine, leucine, lysine, methionine, phenylalanine, proline, serine, taurine, threonine, tryptophan, tyrosine, valine, or combinations thereof.

As used herein, "animal" includes, but is not limited to, mammals, which include but is not limited to, rodents, aquatic mammals, domestic animals such as dogs and cats, farm animals such as sheep, pigs, cows and horses, and humans. Wherein the terms "animal" or "mammal" or their plurals are used, it is contemplated that it also applies to any animals that are capable of the effect exhibited or intended to be exhibited by the context of the passage.

As used herein, the term "antioxidant" is understood to include any one or more of various substances such as beta-carotene (a vitamin A precursor), vitamin C, vitamin E, and selenium) that inhibit oxidation or reactions promoted by Reactive Oxygen Species ("ROS") and other radical and non-radical species. Additionally, antioxidants are molecules of slowing or preventing the oxidation of other molecules. Non-limiting examples of antioxidants include carotenoids, coenzyme Q10 ("CoQ10"), flavonoids, glutathione Goji (wolfberry), hesperidine, lactowolfberry, lignan, lutein, lycopene, polyphenols, selenium, vitamin A, vitamin $B_1$, vitamin $B_6$, vitamin $B_{12}$, vitamin C, vitamin D, vitamin E, zeaxanthin, or combinations thereof.

As used herein, a "consistent" viscosity refers to a viscosity of a product or composition that has minimal variation between the viscosity of the product or composition at room temperature, and the viscosity of the product or composition at a refrigerated temperature.

As used herein, "effective amount" is an amount that prevents a deficiency, treats a disease or medical condition in an individual or, more generally, reduces symptoms, manages progression of the diseases or provides a nutritional, physiological, or medical benefit to the individual. A treatment can be patient- or doctor-related.

As used herein, "elderly" means a human that is sixty-five years of age or older, or at least seventy-five years of age or older.

While the terms "individual" and "patient" are often used herein to refer to a human, the present disclosure is not so limited. Accordingly, the terms "individual" and "patient" refer to any animal, mammal or human having or at risk for a medical condition that can benefit from the treatment.

As used herein, non-limiting examples of fish oils include docosahexaenoic acid ("DHA") and eicosapentaenoic acid ("EPA"). DHA and EPA may also be present from a non-fish oil source (e.g., algae, modified plants, etc.).

As used herein, "food grade micro-organisms" means micro-organisms that are used and generally regarded as safe for use in food.

As used herein, "long term administrations" are continuous administrations for more than 6 weeks.

As used herein, "mammal" includes, but is not limited to, rodents, aquatic mammals, domestic animals such as dogs and cats, farm animals such as sheep, pigs, cows and horses, and humans. Wherein the term "mammal" is used, it is contemplated that it also applies to other animals that are capable of the effect exhibited or intended to be exhibited by the mammal.

The term "microorganism" is meant to include the bacterium, yeast and/or fungi, a cell growth medium with the microorganism, or a cell growth medium in which microorganism was cultivated.

As used herein, the term "minerals" is understood to include boron, calcium, chromium, copper, iodine, iron, magnesium, manganese, molybdenum, nickel, phosphorus, potassium, selenium, silicon, tin, vanadium, zinc, or combinations thereof.

"Nutritional compositions," as used herein, are understood to include any number of optional at additional ingredients, including conventional food additives, for example one or more, acidulants, additional thickeners, buffers or agents for pH adjustment, chelating agents, colorants, emulsifies, excipient, flavor agent, mineral, osmotic agents, a pharmaceutically acceptable carrier, preservatives, stabilizers, sugar, sweeteners, texturizers, and/or vitamins. The optional ingredients can be added in any suitable amount.

As used herein, "phytochemicals" or "phytonutrients" are non-nutritive compounds that are found in many foods. Phytochemicals are functional foods that have health benefits beyond basic nutrition, and are health promoting compounds that come from plant sources. As used herein, "Phytochemicals" and "Phytonutrients" refers to any chemical produced by a plant that imparts one or more health benefit on the user. Phytochemicals can be administered by any means, including topically, enterally and/or parenterally. As used herein, non-limiting examples of phytochemicals and phytonutrients include those that are i) Phenolic compounds which include Monophenols (such as: Apiole, Carnosol, Carvacrol, Dillapiole, Rosemarinol); Flavonoids (polyphenols) including Flavonols (such as: Quercetin, Gingerol, Kaempferol, Myricetin, Rutin, Isorhamnetin), Flavanones (such as: Hesperidin, Naringenin, Silybin, Eriodictyol), Flavones (such as: Apigenin, Tangeritin, Luteolin), Flavan-3-ols (such as: Catechins, (+)-Catechin, (+)-Gallocatechin, (−)-Epicatechin, (−)-Epigallocatechin, (−)-Epigallocatechin gallate (EGCG), (−)-Epicatechin 3-gallate, Theaflavin, Theaflavin-3-gallate, Theaflavin-3'-gallate, Theaflavin-3,3'-digallate, Thearubigins), Anthocyanins (flavonals) and Anthocyanidins (such as: Pelagonidin, Peonidin, Cyanidin, Delphinidin, Malvidin, Petunidin), Isoflavones (phytoestrogens) (such as: Daidzein (formononetin), Genistein (biochanin A), Glycitein), Dihydroflavonols, Chalcones, Coumestans (phytoestrogens), and Coumestrol; Phenolic acids (such as: Ellagic acid, Gallic acid, Tannic acid, Vanillin, Curcumin); Hydroxycinnamic acids (such as: Caffeic acid, Chlorogenic acid, Cinnamic acid, Ferulic acid, Coumarin); Lignans (phytoestrogens), Silymarin, Secoisolariciresinol, Pinoresinol and lariciresinol); Tyrosol esters (such as: Tyrosol, Hydroxytyrosol, Oleocanthal, Oleuropein); Stilbenoids (such as: Resveratrol, Pterostilbene, Piceatannol) and Punicalagins; ii) Terpenes (isoprenoids) which include Carotenoids (tetraterpenoids) including Carotenes (such as: α-Carotene, β-Carotene, γ-Carotene, δ-Carotene, Lycopene, Neurosporene, Phytofluence, Phytoene), and Xanthophylls (such as: Canthaxanthin, Cryptoxanthin, Zeaxanthin, Astaxanthin, Lutein, Rubixanthin); Monoterpenes (such as: Limonene, Perillyl alcohol); Saponins; Lipids including: Phytosterols (such as: Campesterol, beta Sitosterol, gamma sitosterol, Stigmasterol), Tocopherols (vitamin E), and omega-3, 6, and 9 fatty acids (such as: gamma-linolenic acid); Triterpenoid (such as: Oleanolic acid, Ursolic acid, Betulinic acid, Moronic acid); iii) Betalains which include Betacyanins (such as: betanin, isobetanin, probetanin, neobetanin); and Betaxanthins (non-glycosidic versions) (such as: Indicaxanthin, and Vulgaxanthin); iv) Organosulfides which include Dithiolthiones (isothiocyanates) (such as: Sulphoraphane); and Thiosulphonates (allium compounds) (such as: Allyl methyl trisulfide, and Diallyl sulfide), Indoles, glucosinolates which include Indole-3-carbinol; sulforaphane; 3,3'-Diindolylmethane; Sinigrin; Allicin; Alliin; Allyl isothiocyanate; Piperine; Syn-propanethial-S-oxide; v) Protein inhibitors which include protease inhibitors; vi) Other organic acids which include Oxalic acid, Phytic acid (inositol hexaphosphate); Tartaric acid; and Anacardic acid; or combinations thereof.

As used herein, a "prebiotic" is a food substance that selectively promotes the growth of beneficial bacteria or inhibits the growth or mucosal adhesion of pathogenic bacteria in the intestines. They are not inactivated in the stomach and/or upper intestine or absorbed in the gastrointestinal tract of the person ingesting them, but they are fermented by the gastrointestinal microflora and/or by probiotics. Prebiotics are, for example, defined by Glenn R. Gibson and Marcel B. Roberfroid, *Dietary Modulation of the Human Colonic Microbiota: Introducing the Concept of Prebiotics*, J. Nutr. 1995 125; 1401-1412. Non-limiting examples of prebiotics include acacia gum, alpha glucan, arabinogalactans, beta glucan, dextrans, fructooligosaccharides, fucosyllactose, galactooligosaccharides, galactomannans, gentiooligosaccharides, glucooligosaccharides, guar gum, inulin, isomaltooligosaccharides; lactoneotetraose, lactosucrose, lactulose, levan. maltodextrins, milk oligosaccharides, partially hydrolyzed guar gum, pecticoligosaccharides, resistant starches, retrograded starch, sialooligosaccharides, sialyllactose, soyoligosaccharides, sugar alcohols, xylooligosaccharides, or their hydrolysates, or combinations thereof.

As used herein, probiotic micro-organisms (hereinafter "probiotics") are food-grade microorganisms (alive, including semi-viable or weakened, and/or non-replicating), metabolites, microbial cell preparations or components of microbial cells that could confer health benefits on the host when administered in adequate amounts, more specifically, that beneficially affect a host by improving its intestinal microbial balance, leading to effects on the health or well-being of the host. See, Salminen S, Ouwehand A, Benno Y, et al., *Probiotics: how should they be defined?*, Trends Food Sci. Technol. 1999:10, 107-10. In general, it is believed that these micro-organisms inhibit or influence the growth and/or metabolism of pathogenic bacteria in the intestinal tract. The probiotics may also activate the immune function of the host. For this reason, there have been many different approaches to include probiotics into food products. Non-limiting examples of probiotics include *Aerococcus, Aspergillus, Bacillus, Bacteroides, Bifidobacterium, Candida, Clostridium, Debaromyces, Enterococcus, Fusobacterium, Lactobacillus, Lactococcus, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Saccharomyces, Staphylococcus, Streptococcus, Torulopsis, Weissella*, or combinations thereof.

The terms "protein;" "peptide," "oligopeptides" or "polypeptide," as used herein; arc understood to refer to any composition that includes, a single amino acids (monomers), two or more amino acids joined together by a peptide bond (dipeptide, tripeptide, or polypeptide), collagen, precursor, homolog, analog, mimetic, salt, prodrug, metabolite, or fragment thereof or combinations thereof. For the sake of clarity, the use of any of the above terms is interchangeable unless otherwise specified. It will be appreciated that polypeptides (or peptides or proteins or oligopeptides) often contain amino acids other than the 20 amino acids commonly referred to as the 20 naturally occurring amino acids, and that many amino acids, including the terminal amino acids, may be modified in a given polypeptide, either by natural processes such as glycosylation and other post-translational modifications, or by chemical modification techniques which are well known in the art. Among the known modifications which may be present in polypeptides of the present disclosure include, but are not limited to acetylation, acylation, ADP-ribosylation, amidation, covalent attachment of a flavanoid or a heme moiety, covalent attachment of a polynucleotide or polynucleotide derivative, covalent attachment of a lipin or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycation, glycosylation, glycosylphosphatidyl inositol ("GPI") membrane anchor formation, hydroxylation, iodination, methylation, myristoylation, oxidation, proteolytic processing, phosphorylation, prenylation, racemization, selenoylation, sulfation, transfer-RNA mediated addition of amino acids to polypeptides such as arginylation, and ubiquitination. The term "protein" also includes "artificial proteins" which refers to linear or non-linear polypeptides, consisting of alternating repeats of a peptide.

Non-limiting examples of proteins include dairy-based proteins, plant-based proteins, animal-based proteins and artificial proteins. Dairy-based proteins include, for example, casein, caseinates (e.g., all forms including sodium, calcium, potassium caseinates), casein hydrolysates, whey (e.g., all forms including concentrate, isolate, demineralized), whey hydrolysates, milk protein concentrate, and milk protein isolate. Plant-based proteins include, for example, soy protein (e.g., all forms including concentrate and isolate), pea protein (e.g., all forms including concentrate and isolate), canola protein (e.g., all forms including concentrate and isolate), other plant proteins that commercially are wheat and fractionated wheat proteins, corn and it fractions including zein, rice, oat, potato, peanut, green pea powder, green bean powder, and any proteins derived from beans, lentils, and pulses.

As used herein, "short term administrations" are preferably continuous administrations for less than 6 weeks As used herein, a "synbiotic" is a supplement that contains both a prebiotic and a probiotic that work together to improve the microflora of the intestine.

As used herein, the terms "treatment," "treat" and "to alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition, such as nitrogen imbalance or muscle loss. The terms "treatment," "treat" and "to alleviate" are also intended to include the potentiation or otherwise enhancement of one or more primary prophylactic or therapeutic measure. The terms "treatment," "treat" and "to alleviate" are further intended to include the dietary management of a disease or condition or the dietary management for prophylaxis or prevention a disease or condition.

As used herein, a "tube feed" is a complete or incomplete nutritional product or composition that is administered to an animal's gastrointestinal system, other than through oral administration, including but not limited to a nasogastric tube, orogastric tube, gastric tube, jejunostomy tube ("J-tube"), percutaneous endoscopic gastrostomy ("PEG"), port, such as a chest wall port that provides access to the stomach, jejunum and other suitable access ports.

As used herein the term "vitamin" is understood to include any of various fat-soluble or water-soluble organic substances (non-limiting examples include vitamin A, Vitamin B1 (thiamine), Vitamin B2 (riboflavin), Vitamin B3 (niacin or niacinamide), Vitamin B5 (pantothenic acid), Vitamin B6 (pyridoxine, pyridoxal, or pyridoxamine, or pyridoxine hydrochloride), Vitamin B7 (biotin), Vitamin B9 (folic acid), and vitamin B12 (various cobalamins; commonly cyanocobalamin in vitamin supplements), vitamin C, vitamin D, vitamin E, vitamin K, folic acid and biotin) essential in minute amounts for normal growth and activity of the body and obtained naturally from plant and animal foods or synthetically made, pro-vitamins, derivatives, analogs.

The thickener formulations can include specific blends of thickeners such as carrageenan, xanthan and starch that maintain a minimum level of elasticity and viscosity over an extended period of time. The thickener formulations can provide nutritional compositions with a designated level of a viscosity. For example, the viscosity can be similar to nectar, honey, pudding, etc.

The skilled artisan will appreciate that there are many types of starches that may be used in accordance with the present disclosure. A non-limiting list of possible starches includes, for example, Thin and Thick® 99 Starch by A. E. Steley Manufacturing Company, Polartex® 06740 by Cargill, Inc., Polartex® 06747 by Cargill Inc., Polartex® 06748 by Cargill Inc., CreamTex® by Cargill Inc., Rezista® by Tate & Lyle, and Firm-Tex® by National Starch and Chemical Company.

In an embodiment, the present disclosure provides a stable thickener formulation including from about 0.03% to about 0.05% by weight of carrageenan and from about 3.45% to about 3.65% by weight of starch. In an embodiment, the carrageenan is about 0.04% by weight and the starch is about 3.54% by weight. The stable thickener formulation can further include a viscosity ranging from about 4000 cps to about 9000 cps.

In yet another embodiment, the present disclosure provides a stable thickener formulation including from about 0.03% to about 0.05% by weight of carrageenan and from about 1.5% to about 4.0% by weight of starch. This stable thickener formulation can provide a viscosity or consistency similar to nectar.

In an embodiment, the carrageenan is present in an amount from about 0.03% to about 0.04% by weight, and the starch is present in an amount from about 1.8% to about 2.0% by weight. In an embodiment, the carrageenan is present in an amount from about 0.03% to about 0.04% by weight, and the starch is present in an amount from about 2.3% to about 2.5% by weight. In an embodiment, the carrageenan is present in an amount from about 0.03% to about 0.04% by weight, and the starch is present in an amount from about 1.5% to about 1.9% by weight. In an embodiment, the carrageenan is present in an amount from about 0.03% to about 0.04% by weight, and the starch is present in an amount from about 2.1% to about 2.4% by weight. In an embodiment, the carrageenan is about 0.04% by weight and the starch is about 1.8% by weight. In an embodiment, the carrageenan is present in an amount of about 0.0325% by weight and the starch is present in an amount from about 1.5% to about 1.9%, or from about 2.1% to about 2.4%.

In still another embodiment, the present disclosure provides a stable thickener formulation including from about 0.03% to about 0.05% by weight of carrageenan and from about 2.2% to about 2.5% by weight of starch. In an embodiment, the carrageenan is about 0.04% by weight and the starch is about 2.36% by weight. This stable thickener formulation can provide a viscosity or consistency similar to honey.

As used herein, the term "stable" means remaining in a state or condition wherein the viscosity is maintained at a relatively constant level (e.g. differing by no more than 15%, preferably not more than 10%) for an extended period of time (e.g., for at least 1 month). Thickener formulations according to embodiments of the present disclosure can be found to be stable when maintained for at least 1 month, and are generally stable from 2 to 3 months or longer.

In another embodiment, the present disclosure provides a stable thickener formulation including from about 0.1% to about 0.14% by weight of xanthan gum and from about 2.5% to about 2.7% by weight of starch. In an embodiment, the xanthan gum is about 0.12% by weight and the starch is about 2.6% by weight. These stable thickener formulations can include a viscosity ranging from about t 100 cps to about 9000 cps.

In an alternative embodiment, the present disclosure provides a stable nutritional composition including one or more nutritional ingredients, from about 0.03% to about 0.05% by weight of carrageenan, and from about 2.2% to about 2.5% by weight of starch. In another embodiment, the present disclosure provides a stable nutritional composition including at least one nutritional ingredient, from about 0.1% to about 0.14% by weight of xantham gum, and from about 2.5% to about 2.7% by weight of starch.

The thickener formulations can be used as part of pre-thickened nutritional compositions that have a viscosity that is maintained over a period of time (e.g., at least 1, 2 or 3 months or more at refrigeration storage temperatures). The nutritional compositions can include any suitable viscosity that is reached and maintained over a specified period of time such as, for example, at least 1 month, at least 2 months, at least 3 months, etc. In an embodiment, the nutritional compositions can include a viscosity ranging from about 250 cps to about 15,000 cps on a Brookfield LTV viscometer. In another embodiment, the nutritional compositions can include a viscosity ranging from about 1100 cps to about 8500 cps. In yet another embodiment, the nutritional compositions could have a viscosity ranging from about 4500 cps to about 8500 cps. In still yet another embodiment, the nutritional compositions could have a viscosity ranging from about 50 to about 1750 mPa 50 s by Rheology measurements at product temperatures from about 4° C. to about 25° C.

In an embodiment, the nutritional composition further includes a source of carbohydrates. Any suitable carbohydrate may be used in the present nutritional compositions including, but not limited to, sucrose, lactose, glucose, fructose, corn syrup solids, maltodextrin modified starch, amylose starch, tapioca starch, corn starch or combinations thereof.

In an embodiment, the nutritional compositions further include a source of fat. The source of fat may include any suitable fat or fat mixture. For example, the fat source may include, but is not limited to, vegetable fat (such as olive oil, corn oil, sunflower oil, rapeseed oil, hazelnut oil, soy oil, palm oil, coconut oil, canola oil, lecithins, and the like) and animal fats (such as milk fat).

In an embodiment, the nutritional composition further includes one or more prebiotics. As used herein, a prebiotic is a selectively fermented ingredient that allows specific changes, both in the composition and/or activity in the gastroinestinal microflora, that confers benefits upon host well-being and health. Non-limiting examples of prebiotics include *acacia* gum, alpha glucan, arabinogalactans, beta glucan, dextrans, fructooligosaccharides, galactooligosaccharides, galactomannans, gentiooligosaccharides, glucooligosaccharides, guar gum, inulin, isomaltooligosaccharides, lactosucrose, lactulose, levan, maltodextrins, partially hydrolyzed guar gum, pecticoligosaccharides, retrograded starch, soyoligosaccharides, sugar alcohols, xylooligosaccharides, or a combination thereof.

In an embodiment, the nutritional composition further includes one or more probiotics. As used herein, probiotics are defined as microorganisms (i.e., dead or live) that could confer health benefits on the host when administered in adequate amounts. Non-limiting examples of probiotics include *Aerococcus, Aspergillus, Bacteroides, Bifidobacterium, Candida, Clostridium, Debaronmyces, Enterococcus, Fusbacterium, Lactobacillus, Lactococcus, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Saccharomyces, Staphylococcus, Streptococcus, Torulopsis, Weissella*, or a combination thereof. If the probiotics are intended to be used alive, the probiotics may be added at the time of consumption of the nutritional composition by a dry mix packet, an oil suspension, or other methods known in the art for the use of live probiotics.

In another embodiment, the nutritional composition further includes one or more amino acids. Non-limiting examples of amino acids include isoleucine, alanine, leucine, asparagine, lysine, aspartate, methionine, cysteine, phenylalanine, glutamate, threonine, glutamine, tryptophan, glycine, valine, proline, serine, tyrosine, arginine, histidine or a combination thereof.

In an embodiment, the nutritional composition further includes one or more synbiotics, fish oils, phytonutrients and/or antioxidants. As used herein, a synbiotic is a supplement that contains both a prebiotic and a probiotic that work together to improve the microflora of the intestine. Non-limiting examples of fish oils include docosahexaenoic acid ("DHA") and eicosapentaenoic acid ("EPA"). Non-limiting examples of phytonutrients include flavanoids and allied phenolic and polyphenolic compounds, terpenoids such as carotenoids, and alkaloids; including curcurmin, limonin, and quercetin. As used herein the term "antioxidant" is preferably understood to include any one or more of various substances (as beta-carotene (a vitamin A precursor), Vitamin C, vitamin E, and selenium) that inhibit oxidation or reactions promoted by Reactive Oxygen Species (ROS) and other radical and non-radical species. Additionally, antioxidants are molecules capable of slowing or preventing the oxidation of other molecules. Non-limiting examples of antioxidants include carotenoids, coenzyme Q10 ("CoQ10"), flavonoids, glutathione Goji (Wolfberry), hesperidine, Lactowolfberry, lignan, lutein, lycopene, polyphenols, selenium, vitamin A, vitamin B1, vitamin B6, vitamin B12, vitamin C, vitamin D, vitamin E, and combinations.

In an embodiment, the nutritional composition further includes one or more vitamins and minerals. Non-limiting examples of vitamins include Vitamins A, B-complex (such as B-1, B-2, B-6 and B-12), C, D, E and K, niacin and acid vitamins such as pantothenic acid and folic acid and biotin. Non-limiting examples of minerals include calcium, iron, zinc, magnesium, iodine, copper, phosphorus, manganese, potassium, chromium, molybdenum, selenium, nickel, tin, silicon, vanadium and boron.

Other optional ingredients can be added to make the nutritional composition sufficiently palatable. For example, the nutritional compositions of the present disclosure can optionally include conventional food additives, such as any of: acidulants, additional thickeners, buffers or agents for pH adjustment, chelating agents, colorants, emulsifiers, excipient, flavor agent, mineral; osmotic agents, a pharmaceutically acceptable carrier, preservatives, stabilizers, sugar, sweeteners, texturizers, and/or vitamin. The optional ingredients can be added in any suitable amount.

In still another embodiment, the present disclosure provides a method for treating a medical condition in a patient. The method comprises administering to the patient a nutritional composition including at leas one nutritional ingredient, from about 0.03% to about 0.05% by weight of carrageenan, and from 1.5% to about 4.0% by weight of starch.

In an embodiment, the medical condition is dysphagia, renal failure, chronic obstructive pulmonary disorders, malabsorption disorders, etc. The patient can be an elderly person. Alternatively, the patient can be any suitable individual or animal in need of medical therapy.

In an embodiment, the nutritional composition is in an administrable form such as pharmaceutical formulations, nutritional formulations, dietary supplements, functional foods, beverage products or a combination thereof.

An embodiment of the present disclosure is intended to include a stable thickener formulation comprising from about 0.03% to about 0.05% by weight of carrageenan and from about 3.45% to about 3.65% by weight of starch; or wherein the carrageenan is about 0.04% by weight and the starch is about 3.54% by weight; or weight of carrageenan and weight of starch in a ratio of about 1:69 to about 1:122; or weight of carrageenan and weight of starch in a ration about 1:75 to about 1:110.

An embodiment of the present discourse is intended to include a stable thickener formulation comprising weight of carrageenan and weight of starch in a ratio of about 1:80 to about 1:100; or weight of carrageenan and weight of starch in a ratio about 1:85 to about 1:90; or weight of carrageenan and weight of starch in a ratio about 1:88.5.

An embodiment of the present disclosure is intended to include a stable thickener formulation comprising from about 0.03% to about 0.05% by weight of carrageenan and from about 1.5% to about 4.0% by weight of starch in a ratio of about 1:34 to about 1:64; or weight of carrageenan and weight of starch in a ratio of about 1:40 to about 1:55; or weight of carrageenan and weight of starch in a ratio of about 1:43 to about 1:50; or weight of carrageenan and weight of starch in a ratio of about 1:45.

An embodiment of the present disclosure is intended to include a stable thickener formulation comprising from about 0.1% to about 0.14% by weight of xanthan gum and from about 2.5% to about 2.7% by weight of starch; or wherein the xanthan gum is about 0.12% by weight and the starch is about 2.6% by weight.

An embodiment of the present disclosure is intended to include a stable thickener formulation comprising weight of xanthan and weight of starch in a ratio of about 1:18 to about 1:27; or weight of xanthan and weight of starch in a ratio of about 1:20 to about 1:23; or weight of xanthan and weight of starch in a ratio of about 1:21.7.

An embodiment of the present disclosure is intended to include a stable thickener formulation as defined herein wherein the viscosity, at refrigerated temperatures, ranges from about 1100 cps to about 9000 cps, or from about 1100 cps to about 6000 cps, or from about 1100 cps to about 4000 cps.

In an embodiment, the present disclosure is intended to include a nutritional composition comprising at least one nutritional ingredient, from about 0.015% to about 0.05% by weight of carrageenan, and from about 1.2% to about 3.65% by weight of starch.

An embodiment of the present disclosure is intended to include a nutritional composition comprising at least one nutritional ingredient, from about 0.03% to about 0.05% by weight of carrageenan, and from about 3.45% to about 3.65% by weight of starch; or wherein the carrageenan is about 0.04% by weight and the starch is about 3.54% by weight.

An embodiment of the present disclosure is intended to include a nutritional composition comprising at least one nutritional ingredient carrageenan and starch, wherein the weight of carrageenan and weight of starch in a ratio of about 1:69 to about 1:122; or the weight of carrageenan and weight of starch in a ratio of about 1:75 to about 1:110 or wherein the weight of carrageenan and weight of starch in a ratio of about 1:80 to about 1:100; or wherein the weight of carrageenan and weight of starch in a ratio of about 1:85 to about 1:90; or wherein the weight of carrageenan and weight of starch in a ratio of about 1:88.5.

An embodiment of the present disclosure is intended to include a stable thickener formulation comprising from about 0.03% to about 0.05% by weight of carrageenan and from about 2.2% to about 2.5% by weight of starch; or wherein the carrageenan is about 0.04% by weight and the starch is about 2.36% by weight.

An embodiment of the present disclosure is intended to include a nutritional composition comprising at least one nutritional ingredient, from about 0.03% to about 0.05% by weight of carrageenan, and from about 1.7% to about 1.9% by weight of starch; or about 0.03% to about 0.05% by weight of carrageenan and from about 2.2% to about 2.5% by weight of starch.

An embodiment of the present disclosure is intended to include a nutritional composition comprising at least one nutritional ingredient, carrageenan and starch, wherein the weight of carrageenan and weight of starch in a ratio of about 1:34 to about 1:64; or wherein the weight of carrageenan and weight of starch in a ratio of about 1:40 to about 1:55; or wherein the weight of carrageenan and weight of starch in a ratio of about 1:43 to about 1:50; or wherein the weight of carrageenan and weight of starch in a ratio of about 1:45.

An embodiment of the present disclosure is intended to include a nutritional composition comprising at least one nutritional ingredient, from about 0.1% to about 0.14% by weight of xanthan gum and from about 2.5% to about 2.7% by weight of starch; or wherein the xanthan gum is 0.12% by weight and the starch is 2.6% by weight.

An embodiment of the present disclosure is intended to include a nutritional composition comprising at least one nutritional ingredient, xanthan and starch, wherein the weight of xanthan and weight of starch in a ratio of about 1:18 to about 1:27; or wherein the weight of xanthan and weight of starch in a ratio of about 1:20 to about 1:23; or wherein the weight of xanthan and weight of starch in a ratio of about 1:21.7.

An embodiment of the present disclosure is intended to include a nutritional composition as defined herein, wherein the viscosity ranging from about 250 cps to about 15,000 cps.

An embodiment of the present disclosure is intended to include a nutritional composition as defined herein, wherein the nutritional ingredient comprises at least one of a carbohydrate, a protein and a fat.

An embodiment of the present disclosure is intended to include a nutritional composition as defined herein, wherein the nutritional ingredient is selected from the group consisting of prebiotics, probiotics, synbiotics, fish oils, phytonutrients, antioxidants, vitamins, minerals and combinations thereof.

An embodiment of the present disclosure is intended to include a nutritional composition as defined herein, wherein the nutritional composition is in an administrable form selected from the group consisting of pharmaceutical formulations, nutritional formulations, dietary supplements, functional foods, beverage products and combinations thereof.

An embodiment of the present disclosure is intended to include a nutritional composition as defined herein, wherein the nutritional composition is a complete nutritional.

An embodiment of the present disclosure is intended to include a nutritional composition as defined herein, wherein the nutritional composition is an incomplete nutritional.

An embodiment of the present disclosure is intended to include a nutritional composition as defined herein, wherein the nutritional composition is for long-term administration.

An embodiment of the present disclosure is intended to include a nutritional composition as defined herein, wherein the nutritional composition is for short-term administration.

An embodiment of the present disclosure is intended to include a method for treating a medical condition in a patient, the method comprising administering to the patient a nutritional composition as herein defined. The medical condition is selected from the group consisting of dysphagia, renal failure, chronic obstructive pulmonary disorders, malabsorption disorders and combinations thereof. The method is further intended to include a patient that is an elderly person.

An embodiment of the present disclosure is intended to include a method for providing nutrition to a patient with dysphagia comprising administering to the patient a nutritional composition selected as defined herein. The method is further intended to include those patients with dysphagia and a medical condition, the medical condition including, but not limited to renal failure, chronic obstructive pulmonary disorders, malabsorption disorders and combinations thereof.

EXAMPLES

By way of example and not limitation, the following examples are illustrative of various embodiments of the present disclosure. The formulations below are provided for exemplification only, and they can be modified by the skilled artisan to the necessary extent, depending on the special features that are looked for.

Example 1

Nutritional Compositions

Example 1 contains Tables 1 and 2, which provide exemplary formulations for thickeners in accordance with embodiments of the present disclosure.

TABLE 1

Nutritional Composition Having a Thickener Formulation

| Nutrients | Per Serving 237 ml | % US RDI Per Serving 237 ml |
|---|---|---|
| Kcalories | 285 | |
| Caloric Density (cal/ml) | 1.21 | |
| Total Protein g | 14.0 | |
| Fat g | 10.0 | |
| CHO g | 35.0 | |
| Fiber g | | |
| % Energy | | |
| Protein | 26 | |
| Fat | 31 | |
| CHO | 49 | |
| Vit A (IU) | 750 | 15.0 |
| Vit C (mg) | 30 | 50.0 |
| Vit D (IU) | 100 | 25.0 |
| Vit E (IU) | 15.0 | 50.0 |
| Vit K (mcg) | 20 | 25.0 |
| B6 (mg) | 1.00 | 50.0 |
| B12 (mcg) | 1.2 | 20.0 |
| Thiamine (mg) | 0.3 | 20.0 |
| Riboflavin (mg) | 0.425 | 25.0 |
| Folic Acid (mcg) | 100.0 | 25.0 |
| Pantothenic Acid (mg) | 2.0 | 20.0 |
| Choline (mg) | 180 | |
| Biotin (mcg) | 60.0 | 20.0 |
| Niacin (mg) | 5.0 | 25.0 |
| Calcium (mg) | 300 | 30.0 |
| Iron (mg) | 4.5 | 25.0 |
| Manganese (mg) | 0.5 | 25.0 |
| Chloride (mg) | 260 | 7.6 |
| Phosphorus (mg) | 150 | 15.0 |
| Iodine (mcg) | 30 | 20.0 |
| Magnesium (mg) | 60 | 15.0 |
| Zinc (mg) | 4.5 | 30.0 |
| Copper (mg) | 0.50 | 25.0 |
| Sodium (mg) | 100 | 4.2 |
| Potassium (mg) | 230 | 5.6 |
| Chromium (mcg) | 24.0 | 20.0 |
| Molybdenum (mcg) | 18.8 | 25.0 |
| Selenium (mcg) | 14 | 20.0 |

TABLE 2

Nutritional Composition Having a Thickener Formulation and High Protein

| Nutrients | Per Serving 237 ml 8 fl. oz. | % US RDI Per Serving 237 ml |
|---|---|---|
| Kcalories | 358 | |
| Caloric Density (cal/ml) | 1.5 | |
| Total Protein g | 18.0 | |
| Fat g | 14.0 | |
| CHO g | 40.0 | |
| % Calories from: | | |
| Protein % | 20 | |
| Fat % | 35 | |
| Carbohydrate % | 45 | |
| Vit A (IU) | 750 | 15.0 |
| Vit C (mg) | 30 | 50.0 |
| Vit D (IU) | 100 | 25.0 |
| Vit E (IU) | 15.0 | 50.0 |
| Vit K (mcg) | 20 | 25.0 |
| B6 (mg) | 1.00 | 50.0 |
| B12 (mcg) | 1.2 | 20.0 |

TABLE 2-continued

Nutritional Composition Having a Thickener Formulation and High Protein

| Nutrients | Per Serving 237 ml 8 fl. oz. | % US RDI Per Serving 237 ml |
|---|---|---|
| Thiamine (mg) | 0.3 | 20.0 |
| Riboflavin (mg) | 0.425 | 25.0 |
| Folic Acid (mcg) | 100.0 | 25.0 |
| Pantothenic Acid (mg) | 2.0 | 20.0 |
| Choline (mg) | 180 | |
| Biotin (mcg) | 60.0 | 20.0 |
| Niacin (mg) | 5.0 | 25.0 |
| Calcium (mg) | 300 | 30.0 |
| Iron (mg) | 4.5 | 25.0 |
| Manganese (mg) | 0.5 | 25.0 |
| Chloride (mg) | 260 | 7.6 |
| Phosphorus (mg) | 180 | 18.0 |
| Iodine (mcg) | 30 | 20.0 |
| Magnesium (mg) | 60 | 15.0 |
| Zinc (mg) | 4.5 | 30.0 |
| Copper (mg) | 0.50 | 25.0 |
| Sodium (mg) | 190 | 7.9 |
| Potassium (mg) | 270 | 7.7 |
| Chromium (mcg) | 24.0 | 20.0 |
| Molybdenum (mcg) | 18.8 | 25.0 |
| Selenium (mcg) | 14 | 20.0 |

Example 2

Experimental Studies

Example 2 summarizes various experiments that have been performed with thickener formulations of the present disclosure. Applicant has performed several experiments to measure viscosities of various nutritional compositions having different formulations, over time, and at different temperatures (e.g., room temperature and refrigeration temperature). In general, the experiments have shown that added certain amounts of carrageenan or xanthan and starch can provide nutritional compositions with a stable viscosity during extended storage time at the same temperature and at different temperatures. Specifically, for example, adding certain amounts of carrageenan or xanthan and starch can minimize viscosity increases in nutritional compositions stored at refrigerated temperatures. The present experiments have also shown that the amount and type of protein contained in the nutritional compositions and, to some extent, the caloric density of the nutritional compositions can play a role in determining the amounts of carrageenan or xanthan and starch required to achieve a minimized viscosity increase in the nutritional compositions.

Figure 1:
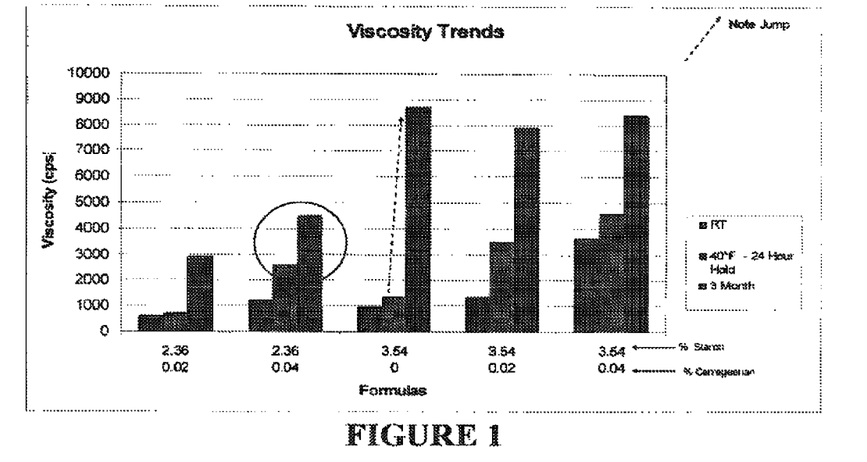
FIG. 1 is a graph showing that carrageenan at 0.04% by weight and starch at 3.54% by weight, and carrageenan at 0.02% by weight and starch at 2.36% by weight reduces the viscosity difference of a formulation between overnight and 3 months storage at 40° F. over other ratios of carrageenan and starch in the formula. The stable viscosity was reached between 24 hours and 1 month.

As discussed above, Applicant has found that the combination of carrageenan and starch in specific amounts in nutritional compositions is able to reduce the difference in viscosity of a formulation over time. For example, as shown in FIG. 1, nutritional compositions having carrageenan at 0.04% by weight and starch at 3.54% by weight, and carrageenan at 0.02% by weight and starch at 2.36% by weight have reduced viscosity differences between an overnight storage and 3 months storage at 40° F. A similar, yet reduced, effect is achieved with lesser amounts of carrageenan, as is also shown by FIG. 1. The stable viscosity was reached between 24 hours and 1 month. After about 24 hours, the thickener formulation had a viscosity in the range of honey refrigerated at 40° F. (e.g., less than 9000 cps).

Figure 2:
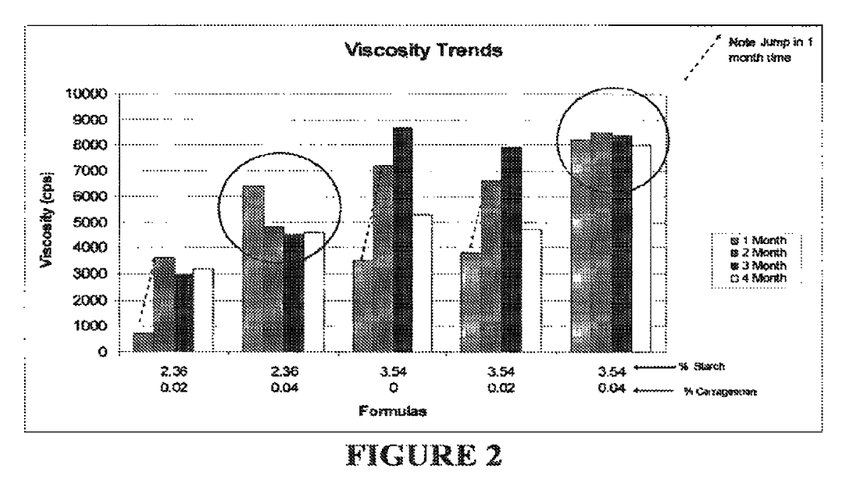
FIG. 2 is a graph showing that carrageenan at 0.04% by weight and starch at 3.54% by weight, and carrageenan at 0.0.02% by weight and starch at 2.36% by weight minimizes the change in viscosity of a formulation between 1 month and 3 months storage at 40° F.

Similarly, and as shown in FIG. 2, carrageenan at 0.04% by weight and starch at 3.54% by weight resulted in a minimal viscosity change between 1 month and 3 months storage at 40° F. As a result, the thickener formulation maintained a stable viscosity for between 1 and 3 months. This is in direct contrast to the increases in viscosity of nutritional compositions having lower amounts of starch and/or lower amounts of carrageenan, as is shown by the broken arrows of FIG. 2.

Figure 3:
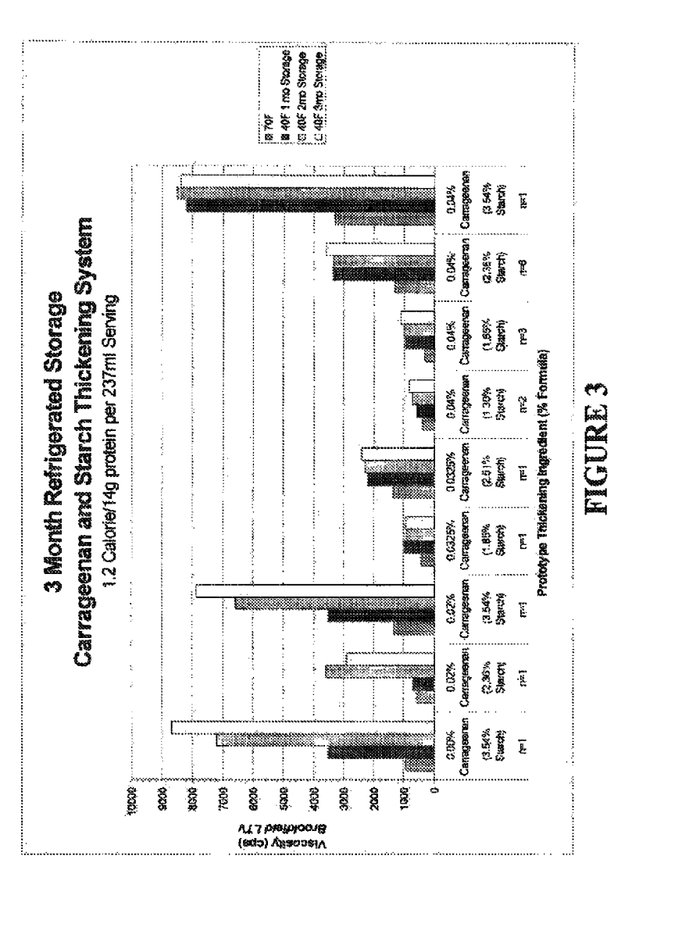
FIG. 3 is a graph showing the viscosities of a nutritional composition having a caloric density of 1.2, 14 g of protein and varying amounts of carrageenan and starch. The graph shows that carrageenan in an amount of about 0.0325% and starch in an amount of at least 1.65% greatly minimized the change in viscosity of a formulation between 1 month and 3 months storage at 40° F.

FIG. 3 also shows minimal viscosity increase in a nutritional composition having a caloric density of 1.2, 14 g of protein, and varying amounts of carrageenan and starch at different temperatures. Specifically, FIG. 3 shows that carrageenan in an amount from at least about 0.0325% and starch in an amount from at least about 1.65% greatly minimizes any change in viscosity of a nutritional composition formulation between 1 month and 3 months storage at 40° F.

Figure 4:
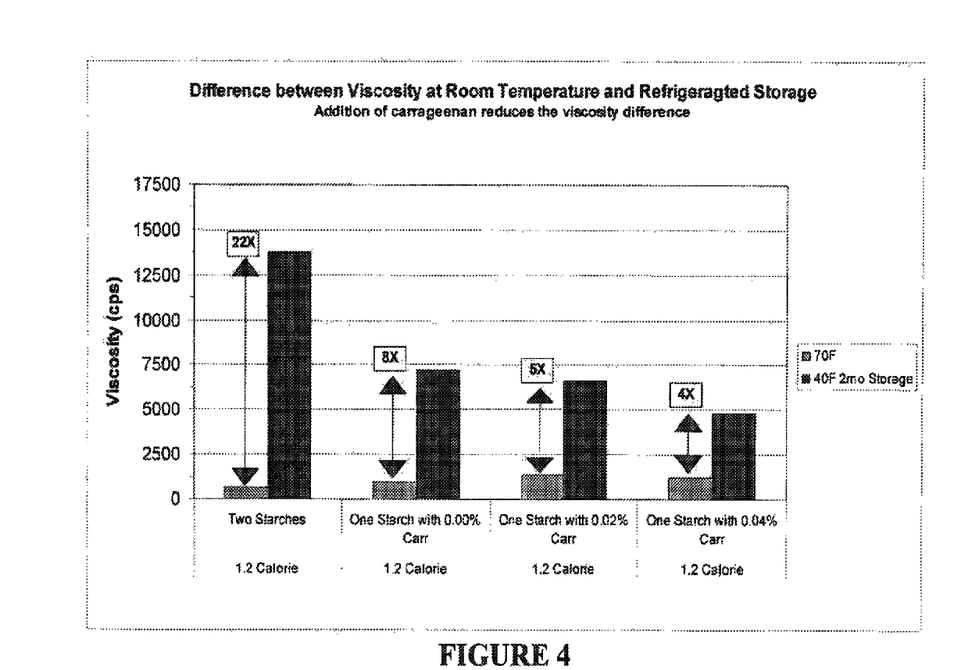
FIG. 4 is a graph showing the reduction in viscosity increase from room temperature storage and refrigerated storage at two months age with the addition of carrageenan.
Figure 5:
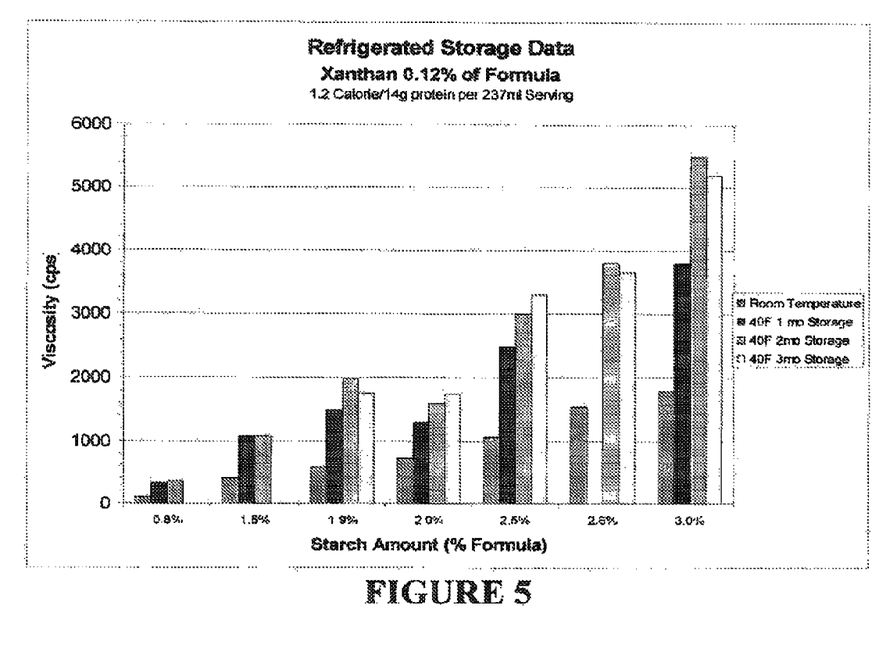
FIG. 5 is a graph showing a minimal viscosity increase from room temperature to a 24 hour hold at 40° F. when using formulations having xanthan gum at 0.12% by weight and various amounts of starch.
Figure 6:
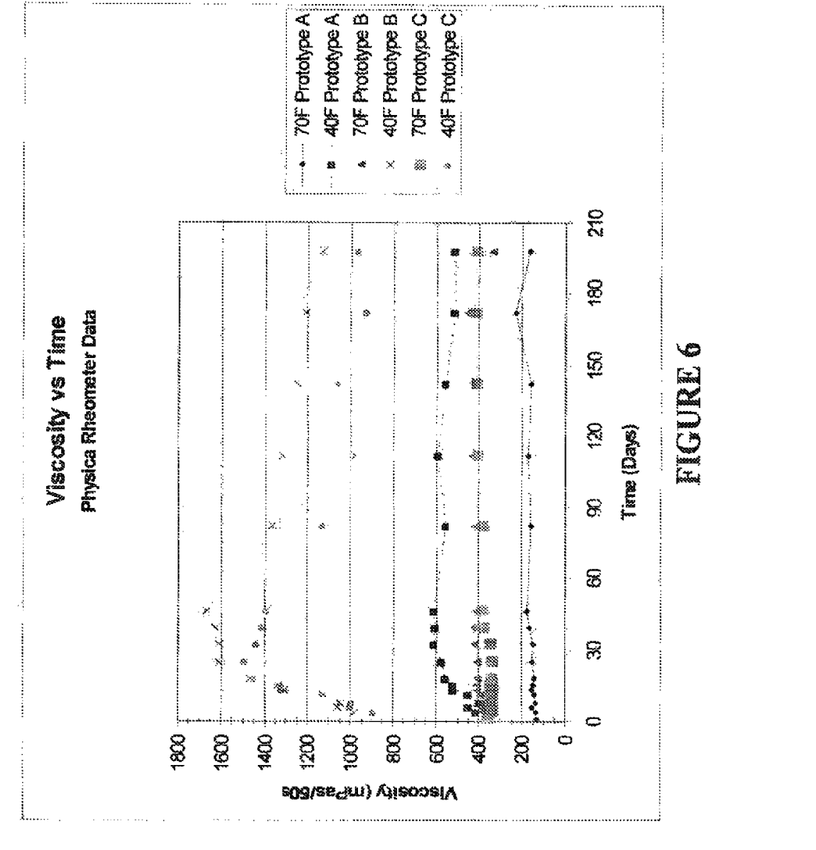
FIG. 6 is a graph showing the viscosity over time, and at two different temperatures, of carrageenan at 0.02%, by weight and starch at 1.8% by weight (Prototype A), of carrageenan at 0.02% by weight and starch at 2.4% by weight (Prototype B), and xanthan gum at 0.12% by weight and starch at 2.6% by weight (Prototype C).

FIGS. 4-6 show the influence of carrageenan and starch on nutritional compositions stored at different temperatures. For example, FIG. 4 shows that the addition of certain amounts of carrageenan to a nutritional composition can reduce a viscosity increase of the nutritional composition when stored at room temperature as opposed to being stored at 40° F. As shown by FIG. 4, a nutritional composition having two starches and no added carrageenan results in a 22-fold increase in viscosity between storage at room temperature and storage at 40° F. The same nutritional composition with one starch and no added carrageenan results in an 8-fold increase in viscosity between storage at room temperature and storage at 40° F. Adding one starch and carrageenan in an amount of 0.02% to the same nutritional composition results in a 5-fold increase in viscosity between storage at room temperature and storage at 40° F. Further, the same nutritional composition with one starch and 0.04% carrageenan results in only a 4-fold increase in viscosity between storage at room temperature and storage at 40° F. As such, FIG. 4 clearly shows that the addition of certain amounts of carrageenan and starch to a nutritional composition can minimize the increase in viscosity of the nutritional composition when stored at room temperature versus 40° F.

In addition to carrageenan, xanthan may be added to nutritional compositions, along with starch, to reduce viscosity increases during storage. For example, FIG. 5 shows a minimal viscosity increase in a nutritional composition from room temperature to a 24 hour hold at 40° F. when using xanthan gum at 0.12% by weight and various amounts of starch. A mixture of about 0.12% by xanthan gum and 2.6% by weight can provide a thickened supplement having a honey consistency. Tables 3-6 further demonstrate the viscosity changes over time at various temperatures when using various concentrations of xanthan gum and starch.

TABLE 3

Viscosity results over time for formulations including 0.295% by weight xanthan gum and 2.36% by weight starch.
Percent Xanthan in formula 0.295
Percent Starch in formula 2.36

| | Viscosity cPs | | |
|---|---|---|---|
| Time | Stored at 43° F. | Stored at 43° F. for 24 hrs | Stored at 70° F. |
| Pre-Process Day of Batching | | | 480 |
| Post Process Day of Batching | | | 2300 |
| 24 hrs | | 5000 | 2800 |

TABLE 3-continued

Viscosity results over time for formulations including 0.295% by weight xanthan gum and 2.36% by weight starch.
Percent Xanthan in formula 0.295
Percent Starch in formula 2.36

| | Viscosity cPs | | |
|---|---|---|---|
| Time | Stored at 43° F. | Stored at 43° F. for 24 hrs | Stored at 70° F. |
| 2 weeks | | 4500 | 2900 |
| 3 weeks | 6500 | | |
| 3 months | 6100 | | 3500 |
| 4 months | 7200 | | 3600 |

TABLE 4

Viscosity results over time for formulations including 0.12% by weight xanthan gum and 0.75% by weight starch.
Percent Xanthan in formula 0.12
Percent Starch in formula 0.75

| | Viscosity cPs | | |
|---|---|---|---|
| Time | Stored at 43° F. | Stored at 43° F. for 24 hrs | Stored at 70° F. |
| Pre-Process Day of Batching | | | 200 |
| Post Process Day of Batching | | | 100 |
| 5 weeks | 330 | 160 | 90 |
| 9 weeks | 360 | | |

TABLE 5

Viscosity results over time for formulations including 0.12% by weight xanthan gum and 1.5% by weight starch.
Percent Xanthan in formula 0.12
Percent Starch in formula 1.5

| | Viscosity cPs | | |
|---|---|---|---|
| Time | Stored at 43° F. | Stored at 43° F. for 24 hrs | Stored at 70° F. |
| Pre-Process Day of Batching | | | |
| Post Process Day of Batching | | | 800 |
| 24 hrs | | | 400 |
| 48 hrs | | 580 | |
| 5 weeks | 1080 | 540 | 340 |
| 9 weeks | 1080 | | 340 |

TABLE 6

Viscosity results over time for formulations including 0.12% by weight xanthan gum and 2.0% by weight starch.
Percent Xanthan in formula 0.12
Percent Starch in formula 2.0

| | Viscosity cPs | | | |
|---|---|---|---|---|
| Time | Stored at 43° F. | Stored at 43° F. for 24 hrs | Stored at 70° F. | Stored at 95° F. |
| Pre-Process Day of Batching | | | 160 | |

TABLE 6-continued

Viscosity results over time for formulations including 0.12% by weight xanthan gum and 2.0% by weight starch.
Percent Xanthan in formula 0.12
Percent Starch in formula 2.0

| | Viscosity cPs | | | |
|---|---|---|---|---|
| Time | Stored at 43° F. | Stored at 43° F. for 24 hrs | Stored at 70° F. | Stored at 95° F. |
| Post Process Day of Batching | | | 720 | |
| 1 week | | 880 | 620 | |
| 2 weeks | | 940 | | |
| 1 month | 1300 | | | |
| 2 months | 1600 | | 700 | |
| 3 months | 1740 | | 800 | 960 |

FIG. 6 shows the viscosity over time, and at different temperatures, of a nutritional composition having (i) carrageenan at 0.02% by weight and starch at about 1.8% by weight ("Prototype A"); (ii) carrageenan at 0.02% by weight and starch at 2.4% by weight ("Prototype B"); and (iii) xanthan gum at 0.12% by weight and starch at about 2.6% by weight ("Prototype C"). As is shown by FIG. 6, the viscosities of the nutritional composition are generally stable over the 210 day period.

Accordingly, the experiments performed using various concentrations of nutritional compositions have shown that adding certain amounts of carrageenan or xanthan and starch can provide nutritional compositions with a stable viscosity during extended storage time at the same temperature and at different temperatures. Specifically, for example, adding certain amounts of carrageenan or xanthan and starch can minimize viscosity increases in nutritional compositions stored at refrigerated temperatures.

Figure 7:
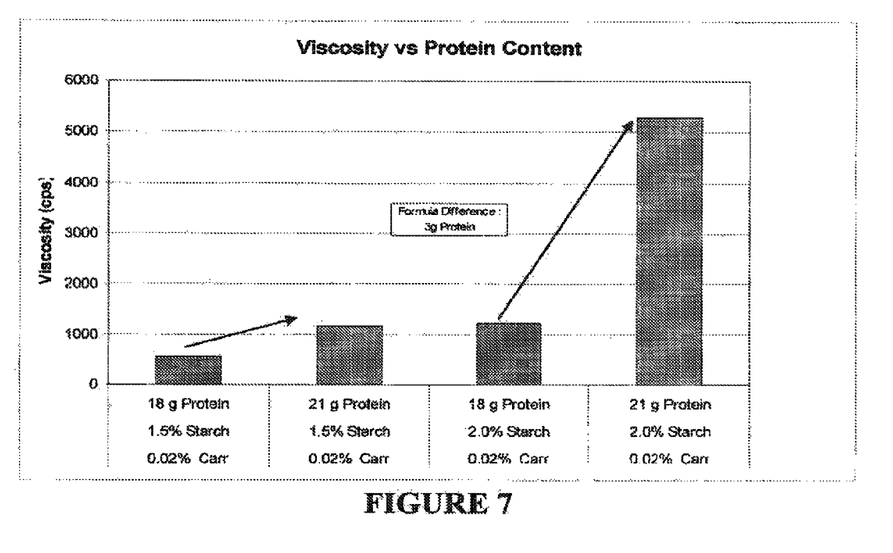
FIG. 7 is a graph showing two nutritional composition formulations and the increase in viscosity of a nutritional composition having 21 g of protein as opposed to 18 g of protein; and the increase in viscosity of a nutritional composition having 1.5% starch as opposed to 2.0% starch.

As mentioned above, however, the present experiments have also shown that the amount and type of protein contained in the nutritional compositions and, to some extent, the caloric density of the nutritional compositions can play a role in determining the amounts of carrageenan or xanthan and starch required to achieve a minimized viscosity increase in the nutritional compositions. For example, FIG. 7 shows viscosity measurements of two nutritional composition formulations. The first composition on the left two bars of FIG. 7 includes about 0.02%) carrageenan and 1.5% starch. The second composition on the right two bars of FIG. 7 includes about 0.02% carrageenan and about 2.0% starch. The bars clearly illustrate the increase in viscosities of the two nutritional compositions having 21 g of protein as opposed to 18 g of protein. Further, the bars of FIG. 7 also clearly illustrate the overall increase in viscosity of a composition having 1.5% starch as opposed to 2.0% starch.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method for treating a medical condition selected from the group consisting of dysphagia, renal failure, chronic obstructive pulmonary disorders, malabsorption disorders, post-stroke, and combinations thereof in a patient, the method comprising administering to the patient a composition including a stable thickener formulation having a viscosity from about 1100 cps to about 9000 cps and selected from the group of:

from about 0.03% to about 0.05% by weight of carrageenan and from about 1.5% to about 4.0% by weight of starch, and at least one nutritional ingredient, and wherein the nutritional ingredient comprises at least one ingredient selected from the group consisting of a carbohydrate, a protein, a fat, prebiotics, probiotics, symbiotics, fish oils, phytonutrients, antioxidants, vitamins, minerals and combinations thereof; and a weight of carrageenan and a weight of starch in a ratio of about 1:69 to about 1:122, and at least one nutritional ingredient, and wherein the nutritional ingredient comprises at least one ingredient selected from the group consisting of a carbohydrate, a protein, a fat, prebiotics, probiotics, symbiotics, fish oils, phytonutrients, antioxidants, vitamins, minerals and combinations thereof.

2. The method of claim 1, wherein the medical condition is dysphagia.

3. The method of claim 1, wherein the medical condition is renal failure.

4. The method of claim 1, wherein the medical condition is a chronic obstructive pulmonary disorder.

5. The method of claim 1, wherein the medical condition is a malabsorption disorder.

6. The method of claim 1, wherein the medical condition is post-stroke.

7. The method of claim 1, wherein the patient is an elderly person.

8. A method for providing nutrition to a patient with dysphagia comprising administering to the patient a composition including a stable thickener formulation having a viscosity from about 1100 cps to about 9000 cps and selected from the group consisting of:

from about 0.03% to about 0.05% by weight of carrageenan and from about 1.5% to about 4.0% by weight of starch, and at least one nutritional ingredient, and wherein the nutritional ingredient comprises at least one ingredient selected from the group consisting of a carbohydrate, a protein, a fat, prebiotics, probiotics, symbiotics, fish oils, phytonutrients, antioxidants, vitamins, minerals and combinations thereof; and a weight of carrageenan and a weight of starch in a ratio of about 1:69 to about 1:122, and at least one nutritional ingredient, and wherein the nutritional ingredient comprises at least one ingredient selected from the group consisting of a carbohydrate, a protein, a fat, prebiotics, probiotics, symbiotics, fish oils, phytonutrients, antioxidants, vitamins, minerals and combinations thereof.

9. The method of claim 8, wherein the patient has a medical condition.

10. The method of claim 9, wherein the medical condition is selected from the group consisting of renal failure, chronic obstructive pulmonary disorders, malabsorption disorders, post-stroke, and combinations thereof.

11. The method of claim 9, wherein the medical condition is renal failure.

12. The method of claim 9, wherein the medical condition is a chronic obstructive pulmonary disorder.

13. The method of claim 9, wherein the medical condition is a malabsorption disorder.

14. The method of claim 9, wherein the medical condition is post-stroke.

15. The method of claim 8, wherein the patient is an elderly person.

16. The method of claim 1, wherein the carrageenan and the starch are present in the formulation in a weight ratio of about 1:75 to about 1:110.

17. A method for treating a medical condition selected from the group consisting of dysphagia, renal failure, chronic obstructive pulmonary disorders, malabsorption disorders, post-stroke, and combinations thereof in a patient, the method comprising administering to the patient a composition including a stable thickener formulation comprising carrageenan, starch and at least one nutritional ingredient, the viscosity of the formulation is from about 300 cps to about 9000 cps, and wherein the nutritional ingredient comprises at least one ingredient selected from the group consisting of a carbohydrate, a protein, a fat, prebiotics, probiotics, symbiotics, fish oils, phytonutrients, antioxidants, vitamins, minerals and combinations thereof, wherein the carrageenan is present in the formulation in an amount about 0.04% by weight and the starch is present in the formulation in an amount about 3.54% by weight.

\* \* \* \* \*